(12) United States Patent
Barak

(10) Patent No.: US 9,937,136 B2
(45) Date of Patent: Apr. 10, 2018

(54) METHODS FOR TREATING RADIATION INDUCED GASTROINTESTINAL TRACT INJURY

(71) Applicant: RDD PHARMA LTD., Tel Aviv (IL)

(72) Inventor: Nir Barak, Tel Aviv (IL)

(73) Assignee: RDD PHARMA LTD., Tel Aviv (IL)

( * ) Notice: Subject to any disclaimer, the term of this patent is extended or adjusted under 35 U.S.C. 154(b) by 0 days.

(21) Appl. No.: 15/036,898

(22) PCT Filed: Nov. 16, 2014

(86) PCT No.: PCT/IL2014/050992
§ 371 (c)(1),
(2) Date: May 16, 2016

(87) PCT Pub. No.: WO2015/071910
PCT Pub. Date: May 21, 2015

(65) Prior Publication Data
US 2016/0279082 A1    Sep. 29, 2016

Related U.S. Application Data

(60) Provisional application No. 61/905,222, filed on Nov. 17, 2013.

(51) Int. Cl.
*A61K 31/185*    (2006.01)
*A61N 5/10*    (2006.01)

(52) U.S. Cl.
CPC .............. *A61K 31/185* (2013.01); *A61N 5/10* (2013.01)

(58) Field of Classification Search
CPC .................................................. A61K 31/185
See application file for complete search history.

(56) References Cited

U.S. PATENT DOCUMENTS

| 7,176,192 | B2 | 2/2007 | Hausheer |
| 2003/0092681 | A1* | 5/2003 | Hausheer |
| 2004/0023925 | A1 | 2/2004 | Chang et al. |

FOREIGN PATENT DOCUMENTS

| WO | 98/16213 A1 | 4/1998 |
| WO | 2005/117851 A1 | 12/2005 |
| WO | 2007/038428 A2 | 4/2007 |

OTHER PUBLICATIONS

National Cancer Institute. "Radiation Therapy for Cancer." (c) 2010. Available from: < https://www.cancer.gov/about-cancer/treatment/types/radiation-therapy/radiation-fact-sheet >.*
Carless, P.A., et al. "Proposal for the inclusion of mesna (sodium 2-mercaptoethane sulfonate) for the prevention of ifosfamide and cyclophosphamide (oxazaphosphorine cytotoxics) induced haemorrhagic cystitis." (c) 2009. Available from: < http://www.who.int/selection_medicines/committees/expert/17/application/mesna_inclusion.pdf >.*
Dictionary.com. "Parenteral." © 2016. Available from: < http://www.dictionary.com/browse/parenteral >.*
MedicineNet.com. "Intraperitoneal." © 2016. Available from: <http://www.medicinenet.com/script/main/art.asp?articlekey=4017 >.*
American College of Gastroneterology. "Enteral and Parenteral Nutrition." © 2016. Available from: < http://patients.gi.org/topics/enteral-and-parenteral-nutrition/ >.*
Pharmacy Tech Study. "Dosage Forms / Routes of Administration." © Jun. 7, 2011. Available from: < http://web.archive.org/web/20110607233026/http://www.pharmacy-tech-study.com/dosage-forms.html >.*
"Topical and Transdermal Drug Products." Pharmacopeial Forum. (May-Jun. 2009), vol. 35, Issue 3, pp. 750-764.*
PharmaTech.com. "Using Excipients in Powder Formulations." © Jan. 7, 2011. Available from: < http://www.pharmtech.com/print/218058?page=full >.*
MediLexicon. "Cachet." © 2012. Available from: < http://www.medilexicon.com/dictionary/13171 >.*
Drugs.com. "Cortifoam." © Mar. 24, 2009. Available from: < http://web.archive.org/web/20090324043944/http://www.drugs.com/pro/cortifoam.html >.*
"Solid Solutions and Dispersions." Particle Sciences. (2012), vol. 3, pp. 1-4. Available from: < http://www.particlesciences.com/news/technical-briefs/2012/sol id-solutions-dispersions.html >.*
U.S. Food and Drug Administration. "Route of Administration." Latest revision date: Jan. 11, 2006. Available from: < http://web.archive.org/web/20110101105507/http://www.fda.gov/Drugs/DevelopmentApprovalProcess/FormsSubmissiomRequirements/ElectronicSubmissions/DataStandardsManualmonographs/ucm071667.htm >.*
Bommarito (2011) Tavocept (BNP7787): a novel chemoprotector/sensitizer and radioprotector/sensitizer. Master of Veterinary Clinical Science thesis, Faculty of the Graduate School University of Missouri (UMI No. 1521029); 81 pages.
Butzner et al., (1996) Butyrate enema therapy stimulates mucosal repair in experimental colitis in the rat. Gut 38(4):568-573.
Godoi et al., (2013) Reappraisal of total body irradiation followed by bone marrow transplantation as a therapy for inflammatory bowel disease. Immunobiology 218(3): 317-324.
Hausheer et al., (2011) Accumulation of BNP7787 in human renal proximal tubule cells. J Pharm Sci 100(9): 3977-3984.
Kumar et al., (1994) Chemotherapy followed by radiotherapy versus radiotherapy alone in locally advanced cervical cancer: a randomized study. Gynecol Oncol 54(3): 307-315.

(Continued)

*Primary Examiner* — Noble E Jarrell
*Assistant Examiner* — John S Kenyon
(74) *Attorney, Agent, or Firm* — Vorys, Sater, Seymour & Pease LLP

(57) ABSTRACT

Methods of preventing, ameliorating and/or treating radiation induced gastrointestinal tract injury comprising the administration of a therapeutically effective amount of Mesna to a patient are provided. Methods for preventing, treating and/or ameliorating gastrointestinal tract injury induced by radiation therapy, alone or in combination with other therapies for diseases or conditions such as gastrointestinal malignancies, urogenital malignancies, gynecologic malignancies, and osteogenic and other sarcomatous malignancies in which pelvic structures are involved.

19 Claims, 1 Drawing Sheet

(56) References Cited

OTHER PUBLICATIONS

Kumar et al., (1998) Neoadjuvant chemotherapy in locally advanced cervical cancer: two randomised studies. Aust NZ J Med 28(3): 387-390.
Mace et al., (2003) Crossover randomized comparison of intravenous versus intravenous/oral mesna in soft tissue sarcoma treated with high-dose ifosfamide. Clin Cancer Res 9(16 Pt 1): 5829-5834.
Plowman et al., (1987) Mesna and total body irradiation. Lancet 1(8525): 167.
Shusterman et al., Effect of the antioxidant Mesna (2-mercaptoethane sulfonate) on experimental colitis. Dig Dis Sci 48(6): 1177-1185.
Verschraagen et al., (2004) Pharmacokinetic behaviour of the chemoprotectants BNP7787 and mesna after an i. v. bolus injection in rats. Br J Cancer 90(8): 1654-1659.
Ypsilantis et al., (2004) Mesna ameliorates intestinal mucosa damage after ifosfamide administration in the rabbit at a dose-related manner. J Surg Res 121(1): 84-91.
MacNaughton (2000) Review article: new insights into the pathogenesis of radiation-induced intestinal dysfunction. Aliment Pharmacol Ther 14(5): 523-528.

\* cited by examiner

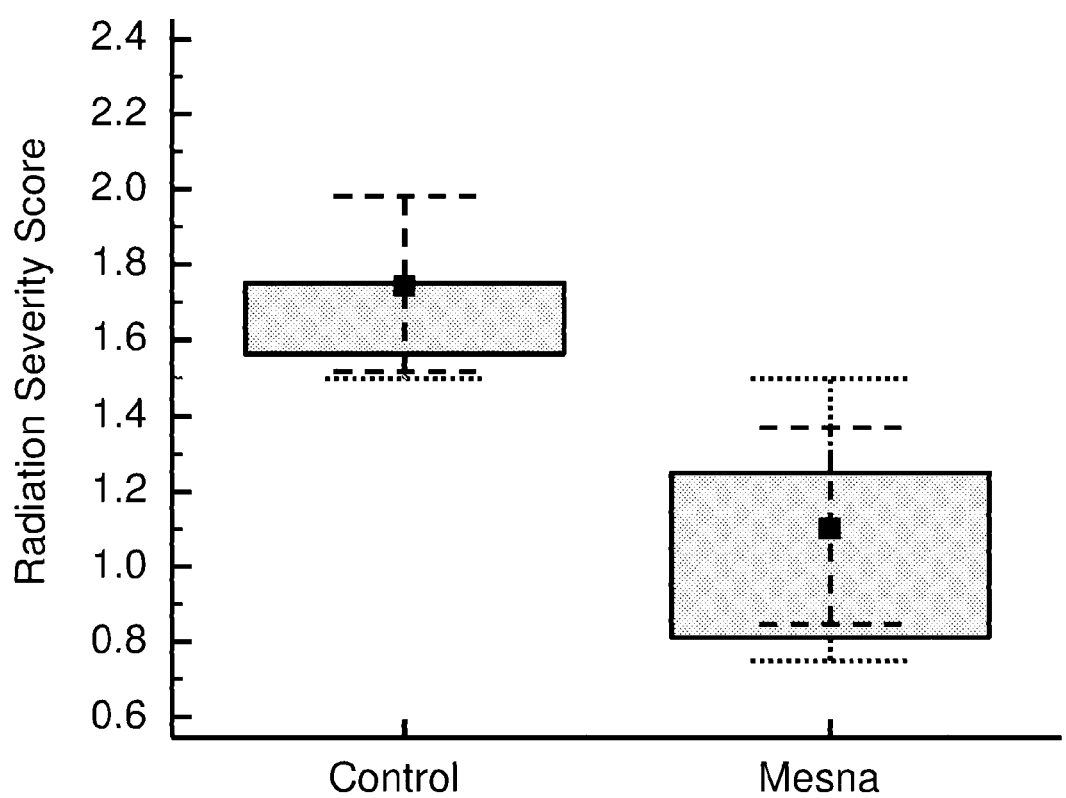

METHODS FOR TREATING RADIATION INDUCED GASTROINTESTINAL TRACT INJURY

FIELD OF THE INVENTION

The present invention relates to methods of treatment, amelioration and/or prevention of gastrointestinal tract injury induced by irradiation. Particularly, the present invention relates to a method of treatment of irradiation-induced gastrointestinal tract injury comprising administering to a subject in need of such treatment a pharmaceutical composition comprising Mesna prior to, during and/or after irradiation.

BACKGROUND OF THE INVENTION

Modern cancer therapy relies strongly on the use of ionizing irradiation, either alone or in combination with surgery or chemotherapy, as a primary strategy for the treatment of malignancies of various types. Ionizing radiation induces multiple and varying biochemical events in various cell types which determine the ability of the cell to survive the radiation challenge.

Treatment of tumors and hyperproliferative diseases with ionizing radiation (hereinafter referred to also as "cancer radiotherapy") is used extensively in cancer therapy. The goal of such treatment is to elicit the destruction of tumor cells and to inhibit tumor cell growth presumably through DNA damage, while attempting to cause minimum damage to non-tumor cells and tissues. Collateral damage to adjacent tissues often limits the radiation doses applied, thus limiting the effectiveness of radiotherapy of certain tumors, such as brain tumors and tumors in the abdominal cavity and the neck.

Mesna (sodium 2-sulfanylethanesulfonate) is a highly water soluble organosulfur compound known to be used as an adjuvant in cancer chemotherapy involving cyclophosphamide and ifosfamide for the prophylaxis of urothelial toxicity.

A few scientific publications describe the use of Mesna in association with colitis or proctitis. Shusterman et al. (Digestive Diseases and Sciences 2003; 48(6):1177-85) discloses treatment of rats with Mesna after exposure to trinitrobenzene sulfonic acid (TNB) as a model of inflammatory bowel disease.

Kumar et al (Gynecol Oncol. 1994; 54(3):307-315) reports a clinical study of patients with squamous cell carcinoma of the cervix who were received various therapies, including, ifosfamide-mesna, following radiotherapy.

The pharmacokinetics (PK) and clinical efficacy of intravenous versus intravenous/oral Mesna in patients receiving ifosfamide for soft tissue sarcoma have been studied by Mace (Clin. Cancer. Res., 2003; 9:5829-5834) where i.v./oral Mesna regimen was found to be at least as uroprotective as the approved i.v. regimen.

WO 2005/117851 discloses methods of prevention, amelioration and treatment of enteritis induced by radiation therapy for the treatment of gastrointestinal malignancies, by administering the anti-inflammatory drug balsalazide to a patient in need thereof.

WO 2007/038428 discloses methods for preventing, treating or ameliorating gastrointestinal (GI) and bladder disorders induced by or associated with chemotherapy or radiation therapy in an animal by administering to the animal active vitamin D compounds. WO 2007/038428 further discloses chemotherapeutic agents including Mesna for the treatment of cancer.

U.S. Patent Application Publication No. 2004/0023925 discloses methods for enhancing the efficacy of conventional cancer therapies such as surgery, chemotherapy and radiation by combining said therapies with the use of a therapeutic material which binds to and interacts with galectins. This publication further discloses pharmaceutical agents that may be used for the combination chemotherapy, among which Mesna is listed as a chemotherapeutic agent.

There remains an unmet need for improved and efficient methods, devoid of adverse systemic effects, for preventing or reducing gastrointestinal tract injury induced by radiation therapy.

SUMMARY OF THE INVENTION

The present invention is directed to methods of treatment, amelioration and/or prevention of gastrointestinal tract injury induced by radiation therapy, said methods comprising administering a therapeutically effective amount of Mesna to a subject in need thereof. In some embodiments, administration of Mesna to a subject in need thereof is prior to, during or after irradiation therapy.

According to one aspect, the present invention provides a method of treating gastrointestinal tract injury induced by ionizing radiation in a subject in need thereof comprising administering to the subject a pharmaceutical composition comprising a therapeutically effective amount of sodium 2-sulfanylethanesulfonate (Mesna) and a pharmaceutically acceptable carrier.

According to some embodiments, administering the pharmaceutical composition is performed prior to, during and/or after the subject's exposure to ionizing radiation. According to other embodiments, the ionizing radiation is a radiation therapy. Each possibility represents a separate embodiment of the present invention.

According to some embodiments, the pharmaceutical composition is administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, twelve weeks or more prior to the radiation exposure. Each possibility represents a separate embodiment of the present invention.

The pharmaceutical composition, in other embodiments, is administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, twelve weeks or more after the cessation of radiation exposure. Each possibility represents a separate embodiment of the present invention.

According to further embodiments, the subject receiving the radiation therapy has a condition selected from the group consisting of: a gastrointestinal malignancy, including colorectal, appendiceal, anal, and small bowel cancers; a urogenital malignancy, including prostate, bladder, testicular, and penile cancers; a gynecological malignancy, including cervical, endometrial, ovarian, vaginal, and vulvar cancers; and osteogenic and other sarcomatous malignancy in which pelvic structures are involved. Each possibility represents a separate embodiment of the present invention.

According to other embodiments, the pharmaceutical composition is administered to the subject once a day, at least twice a day, thrice a day, four times a day or more. Each possibility represents a separate embodiment of the present invention.

According to yet further embodiments, the pharmaceutical composition is administered daily at a dose ranging from about 1 mg of Mesna/kg body weight to about 600 mg of Mesna/kg body weight.

According to other embodiments, the GI tract injury is acute gastrointestinal tract injury. According to a certain embodiment, the acute GI tract injury is colitis. According to a certain embodiment, the acute GI tract injury is proctitis.

According to other embodiments, the pharmaceutical composition is formulated in a form selected from the group consisting of: enemas, gels, rectal foam, suppositories, tablets, suspensions, emulsions, solutions, capsules, pellets, powders, lozenges, sachets, cachets, dispersions, aerosols and ointments. Each possibility represents a separate embodiment of the present invention.

According to other embodiments of the present invention, the pharmaceutical composition is administered in a route selected from the group consisting of: rectal, parenteral, intraperitoneal, intravaginal, oral, intravesical, transmucosal and enteral. Each possibility represents a separate embodiment of the present invention.

According to some embodiments, the radiation therapy is administered in combination with chemotherapy and/or a surgical procedure.

According to another aspect, the present invention provides a method for preventing gastrointestinal tract injury induced by ionizing radiation in a subject comprising, administering to the subject a pharmaceutical composition comprising a therapeutically effective amount of sodium 2-sulfanylethanesulfonate (Mesna) and a pharmaceutically acceptable carrier before, and/or during, and/or after exposure to ionizing radiation.

According to another aspect, the present invention provides use of sodium 2-sulfanylethanesulfonate (Mesna) for the preparation of a medicament for treating or preventing gastrointestinal tract injury induced by ionizing radiation.

According to yet another aspect, the present invention provides a pharmaceutical composition comprising sodium 2-sulfanylethanesulfonate (Mesna) and a pharmaceutically acceptable carrier for treating gastrointestinal tract injury induced by ionizing radiation.

According to yet another aspect, the present invention provides the use of a pharmaceutical composition comprising a therapeutically effective amount of sodium 2-sulfanylethanesulfonate (Mesna) and a pharmaceutically acceptable carrier for the treatment of gastrointestinal tract injury induced by ionizing radiation.

According to some embodiments, the pharmaceutical composition is for use prior to, during and/or after the exposure to ionizing radiation.

According to some embodiments, said use is performed for at least one day prior to the exposure to the radiation therapy.

According to some embodiments, said use is performed for at least five days prior to the exposure to the radiation therapy.

According to some embodiments, said use is performed during the radiation therapy.

According to some embodiments, said use is performed for at least one day after cessation of the radiation therapy.

According to some embodiments, said use is performed for at least fourteen days after cessation of the radiation therapy.

According to some embodiments, said use is performed from at least one day prior to first exposure to the radiation therapy until at least one day after the cessation of radiation therapy.

According to some embodiments, the pharmaceutical composition is for use once a day.

According to some embodiments, the pharmaceutical composition is for use twice a day, thrice a day or four times a day.

According to some embodiments, the pharmaceutical composition is for use at a daily dose ranging from about 1 mg of Mesna/kg body weight to about 600 mg of Mesna/kg body weight.

According to some embodiments, the pharmaceutical composition is in a form selected from the group consisting of: enemas, gels, rectal foam, suppositories, tablets, suspensions, emulsions, solutions, capsules, pellets, powders, lozenges, sachets, cachets, dispersions, aerosols and ointments.

According to some embodiments, the pharmaceutical composition is for use selected from rectal, parenteral, intraperitoneal, intravaginal, oral, intravesical, transmucosal, and enteral.

According to some embodiments, the pharmaceutical composition is for topical use.

According to yet another aspect, the present invention provides a kit for the treatment of gastrointestinal tract injury induced by ionizing radiation, the kit comprises at least one container comprising a pharmaceutical composition comprising a therapeutically effective amount of sodium 2-sulfanylethanesulfonate (Mesna) and a pharmaceutically acceptable carrier; and written instructions for use of said kit for treating gastrointestinal tract injury induced by ionizing radiation.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 shows the preventive effect of Mesna on irradiation-induced gastrointestinal tract injury in mice. Fourteen male C57BL/6 mice were treated with enemas containing either 75 mg/kg body weight of Mesna or saline as a control for 9 days post-exposure to Cs-137 radiation (12 Gy) in the pelvic area. Radiation Injury Histological Scoring (0=no change, 3=severe change) was employed to assess treatment efficacy.

DETAILED DESCRIPTION OF THE INVENTION

Disclosed herein are methods of preventing, treating and ameliorating radiation induced gastrointestinal tract injury by administering a therapeutically effective amount of Mesna to a subject in need thereof.

Radiation damage to the distal or lower end of gastrointestinal tract, namely the anus, anal region, rectum, sigmoid colon, and colon, most commonly occurs with radiation therapy for cancers in the pelvic region such as cancers of the cervix, uterus, prostate, bladder, and testes. Radiation proctosigmoiditis is the most common clinically apparent form of colonic damage after pelvic irradiation. The incidence varies from 5% to 20% in several published series. Clinically, radiation proctitis is seen primarily in those patients exposed to a total pelvic irradiation dose (5000 cGy (rads)), however it may also be observed in lower doses. Patients typically present with symptoms of tenesmus, bleeding, low volume diarrhea, and pain. Rarely, low-grade obstruction or fistulous tracts into adjacent organs may develop.

The principal effects of radiation therapy occur through its interaction with DNA in actively dividing cells. The pathological changes noted after localized radiation therapy to the intestine/colon can be divided into acute and chronic changes. These pathological changes include a loss of lymphocytes in the lamina propria and microscopic damage to mucosal epithelial cells and vascular endothelial cells. These changes manifest as villous blunting and a decrease in crypt regenerative cells. Along with these epithelial changes, marked submucosal edema is seen secondary to increased vascular permeability.

Side effects of these various pelvic radiotherapies cause discomfort and may lead to a decrease in the therapeutic benefit of treatments because of the need for early and unscheduled breaks in therapy. Thus, it would be beneficial to have a treatment that prevents, ameliorates, or otherwise treats the side effects of pelvic therapies.

Mesna (sodium 2-sulfanylethanesulfonate) is an acronym for 2-mercaptoethane sulfonate Na (Na being the symbol for sodium). Mesna is used therapeutically to reduce the incidence of haemorrhagic cystitis and haematuria in patients receiving ifosfamide or cyclophosphamide for cancer chemotherapy. These two anticancer agents, in vivo, may be converted to urotoxic metabolites, such as acrolein. Mesna functions by detoxifying these metabolites via a reaction of its sulfhydryl group with the vinyl group. It also increases urinary excretion of cysteine.

The present disclosure is the first to demonstrate the use of rectally administered Mesna for the treatment of radiation induced gastrointestinal tract injury. Shusterman et al. (ibid) discloses rectal administration of Mesna for the treatment of colitis induced by trinitrobenzene sulfonic acid (TNB) in rats. However TNB induced colitis is an experimental model used to imitate inflammatory bowel disease, and therefore has no relevance to radiation induced GI tissue injury.

Kumar et al (ibid) reports clinical study of 184 patients with squamous cell carcinoma of the cervix who received either two cycles of bleomycin, ifosfamide-mesna, and cis-platinum (BIP) chemotherapy (CT) followed by radiotherapy (RT) or RT alone. Although some of the patients were treated with Mesna prior to radiotherapy, Kumar concludes that no change in the prevalence of proctitis between groups was noted. Similar results were obtained by Kumar in a more recent publication (Aust N Z J Med. 1998; 28(3):387-390).

As aforementioned, Mesna is known to be used as an adjuvant in cancer chemotherapy involving cyclophosphamide and ifosfamide. Clinical researchers have shown that the hydrophilic properties of Mesna, prevent its passage into cells (Mace et al., ibid). This results in efficient renal clearance and avoids any adverse impact on the cytotoxic effects of ifosfamide. After administration, Mesna is rapidly oxidized in the plasma to form dimesna (disodium 2,2-dithiodiethyanesulfonate), which is the predominant circulating form of Mesna. After glomerular filtration, dimesna undergoes reabsorption in the proximal tubules. Before secretion in the distal tubules, one third of the dimesna is rapidly converted back to the active thiol, mesna, by glutathione reductase in the cytoplasm of the distal tubular epithelial cells. Mesna then readily detoxifies urinary 4-hydroxyifosfamide metabolites and acrolein.

The present invention provides a method for treating a radiation induced gastrointestinal tract injury in a subject in need thereof said method comprising the step of administering to said subject a therapeutically effective amount of Mesna or a pharmaceutical composition comprising same and a pharmaceutically acceptable carrier, thereby treating a gastrointestinal tract injury induced by radiation therapy.

The present invention further provides a pharmaceutical composition comprising a therapeutically effective amount of sodium 2-sulfanylethanesulfonate (Mesna) and a pharmaceutically acceptable carrier for the treatment of gastrointestinal tract injury induced by ionizing radiation.

The present invention further provides a kit for the treatment of gastrointestinal tract injury induced by ionizing radiation, the kit comprises at least one container comprising a pharmaceutical composition comprising a therapeutically effective amount of sodium 2-sulfanylethanesulfonate (Mesna) and a pharmaceutically acceptable carrier; and written instructions for use of said kit for treating gastrointestinal tract injury induced by ionizing radiation.

The kit may further comprise instructions for coordinating the administration of said pharmaceutical composition with radiotherapy. The kit may further comprise a notice in the form described by a governmental agency regulating the manufacture, use or sale of pharmaceuticals or biological products, which notice reflects approval by the agency of manufacture, use or sale for human administration.

The term "pharmaceutically acceptable" means approved by a regulatory agency of the Federal or a state government or listed in the U.S. Pharmacopeia or other generally recognized pharmacopeia for use in humans and animals. The term "carrier" refers to a diluent, adjuvant, excipient, or vehicle with which the active agent is administered. Such pharmaceutical carriers may be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is one of the preferred carriers when the pharmaceutical composition is administered intravenously. Saline solutions and aqueous dextrose and glycerol solutions may also be employed as liquid carriers, particularly for injectable solutions. Suitable pharmaceutical excipients include, but not limited to starch, glucose, lactose, sucrose, gelatin, malt, rice, flour, chalk, silica gel, sodium stearate, glycerol monostearate, talc, sodium chloride, dried skim milk, propylene glycol, water, ethanol and the like. The composition, if desired, may also contain minor amounts of wetting or emulsifying agents, or pH buffering agents, such as, acetates, citrates or phosphates. Antibacterial agents, such as, benzyl alcohol or methyl parabens; antioxidants, such as, ascorbic acid or sodium bisulfite; chelating agents, such as, ethylenediaminetetraacetic acid; and agents for the adjustment of tonicity, such as, sodium chloride or dextrose are also envisioned.

The terms "ionizing radiation" or "radiation" as used herein refer to photons having enough energy to ionize a bond, such as, $\alpha$, $\beta$ and $\gamma$ rays from radioactive nuclei and x-rays. Other types of radiation, which may damage normal tissue while irradiating the tumor tissue, are laser irradiation, microwave irradiation, ultraviolet radiation, infrared radiation or ultrasonic thermotherapy; all are encompassed in the present invention. The applied radiation may be used locally, to a specific organ or tissue or it may be total body radiation.

Sources of radiation exposure include, but are not limited to, radiotherapy, nuclear warfare, nuclear reactor accidents, and improper handling of research or medical radioactive materials.

Radiation therapy and radiotherapy are used interchangeably herein and include external irradiation and internal irradiation, also referred to as brachytherapy, intracavitary brachytherapy, or interstitial brachytherapy. Radiation sources and types contemplated include pure Gamma, pure Beta and mixed irradiations.

As used herein "injury" or "damage" refers to GI tissue damage or disorders characterized by a recognized etiologic agent or agents, an identifiable group of signs and symptoms, including adverse effects, unwanted effects, undesired effects, or abnormal signs or symptoms or consistent anatomical alterations.

Irradiation often causes acute radiation gastrointestinal tract injury. Symptoms may include diarrhea, proctitis, stool incontinence, loose stool, increased defecations per day, tenesmus, mucous production, abdominopelvic pain, and ped-rectal discomfort. Without wishing to be bound by any theory or mechanism, acute radiation gastrointestinal tract injury results largely from irritation of the sigmoid colon, rectum and other parts of the digestive tract. Symptoms may develop during or after the radiation exposure, depending on the person's health, the duration and/or the irradiation dose.

Additionally, irradiation, may damage a person's genetic material (DNA) causing chronic (delayed) disorders, such as cancer and other illnesses. Intestinal cells are multiplying quickly and therefore are more susceptible to being harmed by radiation than organs in which cells multiply more slowly.

The term "gastrointestinal tract injure" as used herein, refers to any injury, damage or disorder associated with any part of the GI tract, including the mouth, esophagus, stomach, small intestine, large intestine, and rectum. GI disorders include, but are not limited to, nausea, vomiting, diarrhea, GI bleeding, esophagitis, stomatitis, xerostomia, mucositis, pancreatitis, colitis, proctitis, fibrosis, constipation, abdominal cramps, abdominal pain, dehydration, malabsorption, anorexia and weight loss.

As used herein the term "colitis" refers to an inflammation of the large intestine—colon, caecum and rectum. The term "colitis", as used herein, is meant to include both acute and chronic colitis.

In the present invention, the radiation induced gastrointestinal tract injury may be caused by a combination of radiation therapy with chemotherapy and/or surgical procedures. In general, subjects who may benefit from treatment with Mesna include those who are scheduled to begin or those who are in the process of undergoing radiation therapy, particularly in the pelvic region.

According to other embodiments of the present invention, the radiation induced gastrointestinal tract injury is caused by non-therapeutic radiation exposure to a radiation source such as nuclear warfare, nuclear reactor accidents, and improper handling of research and/or medical radioactive materials.

As used herein, the terms "chemotherapy" and "chemotherapeutic agents" are used interchangeably and refer to chemotherapeutic agents or drugs exhibiting anti-cancer effects used in the treatment of malignancies.

The term "treating" as used herein includes the diminishment, alleviation, or amelioration of at least one symptom associated with, or caused by, the exposure to radiation. The term "treating" as used herein also includes preventative (e.g., prophylactic), palliative and curative treatment. Thus, the present invention further encompasses a method for preventing formation of gastrointestinal tract injury induced by radiation. The present invention also provides a method for reducing the risk of pathology resulting from said gastrointestinal tract injury induced by radiation. The prevention may be complete, e.g., total absence of GI tract injury induced by radiation. The prevention may also be partial, such that the GI tract injury induced by radiation is less than that which would have occurred without administering a pharmaceutical composition comprising Mesna.

Also provided herein are methods which are useful for improving tissue function in a subject having, or at risk of having tissue toxicity due to irradiation. Thus, the present invention also provides methods for preventing tissue toxicity and/or damage due to irradiation.

The term "a therapeutically effective amount" as used herein refers to an amount of an agent which is effective, upon single or multiple dose administration to the subject, in providing a therapeutic benefit to the subject and/or in preventing tissue injury or damage. In one embodiment, the therapeutic benefit is inhibiting or ameliorating symptoms of radiation-induced gastrointestinal tract injury.

As used herein, the term "administering" refers to bringing mammalian cells in contact with the compound or composition of the present invention.

Subjects who may particularly benefit from the treatment disclosed herein include those who are or may be susceptible to gastrointestinal tract injury. For example, the subjects are about to undergo, undergo, or have undergone radiation therapy.

Also included are subjects who are, or who may be, susceptible to gastrointestinal tract injury. Subjects may be suffering from, for example and not limited to, gastrointestinal malignancies, including colorectal, rectal, appendiceal, anal or small bowel cancers; urogenital malignancies, including prostate, bladder, testicular, or penile cancers; gynecologic malignancies, including cervical, endometrial, ovarian, vaginal, or vulvar cancers; or osteogenic and other sarcomatous malignancies in which pelvic structures are involved.

According to one aspect, the present invention provides a method for treating a subject in need thereof with Mesna, wherein identifying the subject in need of such treatment can be the domain of a health care professional and be subjective (e.g. opinion) or objective (e.g. measurable by a test or diagnostic method). Alternatively, subjects may self-administer Mesna based on self discretion.

Mesna may be used in various treatment regimens. The administration regimen may be determined by a care-giver or a healthcare professional depending on the severity of the condition or depending on the treatment type (e.g. irradiation therapy, chemotherapy etc.), age, weight, type of treatment, rout of administration etc.

The administration schedule may be initiated prior to, and/or during, and/or after the irradiation treatment; alone or in conjunction with other therapies. The administration schedule may be once-daily, twice-daily, thrice daily, four times a day, once-weekly or once-monthly. In addition, the administration may be continuous, i.e., every day, or intermittently. The terms "intermittent" or "intermittently" as used herein means stopping and starting at either regular or irregular intervals. For example, intermittent administration may be administration one to six days per week or it may mean administration in cycles (e.g. daily administration for two to eight consecutive weeks, then a rest period with no administration for up to one week) or it may mean administration on alternate days. Some particularly preferred embodiments of the present invention comprise administering the Mesna once daily to the subject as it may, for example, minimize the side effects and increase patient compliance.

Dosages, according to certain embodiments, of the pharmaceutical composition may vary. The administered daily dose may range from between about 1 mg of Mesna/kg body weight to about 600 mg of Mesna/kg body weight. For example, a dose of 300 mg/kg body weight may be administered to a subject twice daily. Other appropriate dosages, for methods according to this invention, may be determined by health care professionals or by the subject. The precise suitable dose to be employed also depends on numerous factors such as weight, age, health, sex, route of administration, the amount (dose) and duration of the irradiation exposure, the progression of the disease/disorder/medical condition of the subject and should be decided by the practitioner based on patient circumstances.

Typically, dosage in the range of 6 mg/kg body weight may be used. Exemplary, non-limiting amounts of Mesna include 1 mg/kg body weight, 2 mg/kg body weight, 5 mg/kg body weight, 10 mg/kg body weight, 20 mg/kg body weight, 50 mg/kg body weight, 60 mg/kg body weight, 75 mg/kg body weight, 100 mg/kg body weight, 200 mg/kg body weight, 300 mg/kg body weight and 600 mg/kg body weight. Each possibility represents a separate embodiment of the present invention.

A pharmaceutically acceptable carrier may be any material with which the active ingredient is formulated to facilitate administration. A carrier may be a solid, semi-solid or a liquid, including a material which is normally gaseous but which has been compressed to form a liquid, and any of the carriers normally used in formulating pharmaceutical compositions. Typically, compositions according to the invention contain 0.5 to 95% by weight of active ingredient.

Auxiliary components such as tablet disintegrants, solubilisers, preservatives, antioxidants, surfactants, viscosity enhancers, coloring agents, flavoring agents, pH modifiers, sweeteners or taste-masking agents may also be incorporated into the composition. Suitable coloring agents include, but are not limited to, red, black and yellow iron oxides and 1-D & C dyes such as FD & C blue No. 2 and FD & C red No. 40 available from Ellis & Everard. Suitable flavoring agents include, but are not limited to, mint, raspberry, licorice, orange, lemon, grapefruit, caramel, vanilla, cherry and grape flavors and any combinations thereof. Suitable pH modifiers include, but are not limited to, citric acid, tartaric acid, phosphoric acid, hydrochloric acid and maleic acid. Suitable sweeteners include, but are not limited to, aspartame, acesulfame K and thaumatin. Suitable taste-masking agents include, but are not limited to, sodium bicarbonate, ion-exchange resins; cyclodextrin inclusion compounds, adsorbates or microencapsulated actives. Each possibility represents a separate embodiment of the present invention.

The Mesna may be administered, in some embodiments, directly to the gastrointestinal tract or part thereof. In specific embodiments, the active agent is delivered to the large intestine. In specific embodiments, Mesna is administered in an enema form, a rectal foam form, a rectal gel form or in suppository form. Each possibility represents a separate embodiment of the present invention.

Alternative suitable routes of administration of the compounds and compositions of the present invention include, but are not limited to, rectal, parenteral, intraperitoneal, intravaginal, oral, intravesical, transmucosal, and enteral administration routes or any combination thereof. Each possibility represents a separate embodiment of the present invention.

Mesna may be formulated as, for example, enemas, gels, rectal foam tablets, suppositories suspensions, emulsions, solutions, capsules, pellets, powders, lozenges, sachets, cachets, dispersions, aerosols and ointments. Each possibility represents a separate embodiment of the present invention.

In particular embodiments, subjects in need thereof include subjects that will undergo radiation therapy, either alone or in combination with other pelvic related therapies that could induce gastrointestinal tract injury. This need may be apparent prior to undergoing radiation therapy with chemotherapy, a pelvic surgical procedure or a combination of therapies; subjects undergoing radiation therapy, chemotherapy, a pelvic surgical procedure or a combination of therapies; and subjects undergoing post radiation therapy, chemotherapy, a pelvic surgical procedure, or a combination of therapies. Each possibility represents a separate embodiment of the present invention. For example, subjects may be about to undergo, may be undergoing, or have undergone radiation therapy in combination with chemotherapy or a surgical procedure.

According to certain embodiments, Mesna may be administered prior to radiotherapy. Mesna may be administered, for example, at least one day prior to the subject's first dose of radiotherapy, at least five days prior to the subject's first dose of radiotherapy, during radiation therapy, for at least one day after the cessation of radiation therapy, for thirty days after the cessation of radiation therapy. Administration at least five days prior to the therapy includes administration daily, every day prior to the pelvic therapy, administration on a majority of days prior the therapy, administration on the day of treatment or no administration on the day of treatment. Each possibility represents a separate embodiment of present invention.

For subjects undergoing multiple therapies, Mesna may be administered, for example, at least one day prior to the subject's first dose of radiotherapy, chemotherapy, and/or prior to undergoing a surgical procedure; at least five days prior to the subject's first dose of radiotherapy, chemotherapy, and/or prior to undergoing a surgical procedure; during radiation therapy, chemotherapy, and/or the surgical procedure; at least one day after the cessation of radiation therapy, chemotherapy, or after the surgical procedure; for fourteen days after the cessation of radiation therapy, chemotherapy, or after the surgical procedure. Each possibility represents a separate embodiment of present invention.

It is often preferable to administer Mesna to a subject prior to treatment, during treatment, as well as after the cessation of treatment. For example, Mesna may be administered daily from at least one day prior to the first dose of radiotherapy, chemotherapy, and/or prior to undergoing the surgical procedure until at least one day after the cessation of radiation therapy, chemotherapy, or the surgical procedure.

Indications include a subject receiving radiotherapy alone or in combination with chemotherapy, and/or surgical procedure as a result of treatment for cancer of the cervix, prostate, appendix, colon, intestine, rectum, or other gastrointestinal malignancy, or prostatectomy. Each possibility represents a separate embodiment of present invention.

According to certain embodiments, Mesna may be administered in combination with other compounds, including for example, chemotherapeutic agents, anti-inflammatory agents, anti-pyretic agents radiosensitizing agents, radioprotective agents, urologic agents, anti-emetic agents, and/or anti-diarrheal agents for example, cisplatin, carboplatin, docetaxel, paclitaxel, flurouracil, capecitabine, gemcitabine, irinotecan, topotecan, etoposide, mitomycin, gefitinib, vincristine, vinblastine, doxorubicin, cyclophosphamide, celecoxib, rofecoxib, valdecoxib, ibuprofen, naproxen, ketoprofen, dexamethasone, prednisone, prednisolone, hydrocortisone, acetaminophen, misonidazole, amifostine, tamsulosin, phenazopyridine, ondansetron, granisetron, alosetron, palonosetron, promethazine, prochlorperazine, trimethobenzamide, aprepitant, diphenoxylate with atropine, and/or loperamide. Each possibility represents a separate embodiment of present invention.

The methods disclosed herein are also useful for protecting a subject against radiation induced gastrointestinal tract injury by administering to a subject in need thereof a therapeutically effective amount of Mesna. For example, prophylactic doses may be administered prior to a patient undergoing radiation.

The methods disclosed herein are useful for protecting a subject against radiation induced injury to the mucosa of the colon, as well as against radiation induced colorectal inflammation by administering to a subject in need thereof a therapeutically effective amount of Mesna.

Definitions

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "about" refers to plus/minus 10% of the value stated.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Example 1: Effect of Mesna on Radiation-Induced Gastrointestinal Tract Injury

The present invention is based in part on the unexpected finding that the rectal administration of Mesna to mice experiencing radiation induced gastrointestinal tract injury, reduces symptoms of the condition. In the present study, 14 male C57BL/6 mice were randomly divided into two groups—treatment group and control group. The pelvic area (containing the ano-rectal part of the intestine) of each mouse was exposed to a Cs-137 source and irradiated over 2 minutes at a rate of 6 Gy/min (a 12 Gy dose). Starting from the day of irradiation and for a period of 9 days, mice in the treatment group received enemas containing Mesna at a dose of 75 mg/kg body weight. Animals in the control group received saline enemas as a control. Animals were sacrificed nine days post irradiation and gross necropsy of the anus, rectum and colon was performed and documented by high resolution color pictures. Specimens of 7 cm of the intestinal tract starting from the muco-cutaneous junction up to the colon were collected and fixed for histological evaluation in formalin, according to pathology department guidelines. FIG. 1 presents the statistical mean (black square) with the corresponding standard error (dashed line) and standard deviation (dotted line) of mucosal alteration scoring (0=no change, 3=severe change) which was employed to evaluate the efficacy of the different treatments, where the rectangles mark an area encompassing 80% of the scores for each of the groups. Surprisingly, the results showed that the mucosal alteration score was significantly reduced in animals treated with Mesna enemas.

The success of rectally administered Mesna to the treatment of radiation induced gastrointestinal tract injury may be attributed to the hydrophilic properties of Mesna, which ensure that this compound will stay in the lumen of the lower gastrointestinal tract and will not enter the gastrointestinal cells. Furthermore, lack of absorption of Mesna will not allow its conversion to dimesna, the active form of the drug for conventional treatment of cyclophosphamide and ifosfamide. Therefore Mesna is suitable and advantageous for treating and/or preventing radiation complications in the GI tract, as the present invention discloses.

Although the invention is described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A method of treating gastrointestinal tract injury induced by ionizing radiation in a subject comprising administering to the subject a pharmaceutical composition comprising a therapeutically effective amount of sodium 2-sulfanylethanesulfonate (Mesna) and a pharmaceutically acceptable carrier through rectal administration.

2. The method of claim 1, wherein administering the pharmaceutical composition is performed prior to, during and/or after the subject's exposure to ionizing radiation.

3. The method of claim 2, wherein the ionizing radiation is a radiation therapy.

4. The method of claim 2, wherein administering the pharmaceutical composition is performed for at least one day prior to the exposure of the subject to the radiation therapy.

5. The method of claim 2, wherein administering the pharmaceutical composition is performed for at least five days prior to exposure of the subject to radiation therapy.

6. The method of claim 2, wherein administering the pharmaceutical composition is performed during the radiation therapy.

7. The method of claim 2, wherein administering the pharmaceutical composition is performed for at least one day after the cessation of the radiation therapy.

8. The method of claim 2, wherein administering the pharmaceutical composition is performed for at least fourteen days after the cessation of the radiation therapy.

9. The method of claim 2, wherein administering the pharmaceutical composition is performed from at least one day prior to first exposure of the subject to the radiation therapy until at least one day after the cessation of radiation therapy.

10. The method of claim 2, wherein the subject receiving radiation therapy has a condition selected from the group consisting of: a gastrointestinal malignancy, urogenital malignancy, gynecological malignancy and other sarcomatous malignancy.

11. The method according to claim 1, wherein the pharmaceutical composition is administered to the subject once a day.

12. The method according to claim 1, wherein the pharmaceutical composition is administered to the subject twice a day, thrice a day or four times a day to the subject.

13. The method according to claim 1, wherein the pharmaceutical composition is administered daily at a dose ranging from about 1 mg of Mesna/kg body weight to about 600 mg of Mesna/kg body weight.

14. The method according to claim 1, wherein the gastrointestinal tract injury is acute gastrointestinal tract injury.

15. The method of claim 14, wherein the injury is colitis or proctitis.

16. The method according to claim 1, wherein the pharmaceutical composition is formulated in a form selected from the group consisting of: enemas, gels, rectal foam, suppositories, tablets, suspensions, emulsions, solutions, capsules, pellets, powders, sachets, cachets, dispersions, aerosols and ointments.

17. The method of claim 3, wherein the radiation therapy is performed in combination with chemotherapy and/or a surgical procedure.

18. A method for preventing gastrointestinal tract injury induced by ionizing radiation in a subject comprising administering, through rectal administration, to the subject a pharmaceutical composition comprising a therapeutically effective amount of sodium 2-sulfanylethanesulfonate (Mesna) and a pharmaceutically acceptable carrier before, during, and/or after exposure the subject to the ionizing radiation.

19. The method of claim 18, wherein the ionizing radiation is radiation therapy.

* * * * *